United States Patent [19]

Combourieu et al.

[11] Patent Number: 4,631,277
[45] Date of Patent: Dec. 23, 1986

[54] HEXAHYDRODIBENZODIOXANE COMPOUNDS AND PHARMACEUTICAL COMPOSITIONS

[75] Inventors: Michel Combourieu, Aurillac; Yvon Bernet, Jussac; Jean-Claude Laigle; Nadine Simbille, both of Aurillac, all of France

[73] Assignee: Riom Laboratories C.E.R.M. "RL-C.E.R.M." S.A., Riom, France

[21] Appl. No.: 753,866

[22] Filed: Jul. 11, 1985

[30] Foreign Application Priority Data

Jul. 13, 1984 [FR] France ............... 84 11174

[51] Int. Cl.$^4$ ............ A61K 31/335; A61K 31/535; C07D 319/24; C07D 413/12
[52] U.S. Cl. ............ 514/239; 544/148; 546/197; 548/526; 549/359; 514/321; 514/422; 514/452
[58] Field of Search .......... 544/148; 546/197; 548/526; 549/359; 514/239, 321, 422, 452

[56] References Cited
FOREIGN PATENT DOCUMENTS
146579 9/1983 Japan .

Primary Examiner—Robert W. Ramsuer
Attorney, Agent, or Firm—William M. Blackstone

[57] ABSTRACT

The invention is dealing with antispasmodic compounds of the formula I

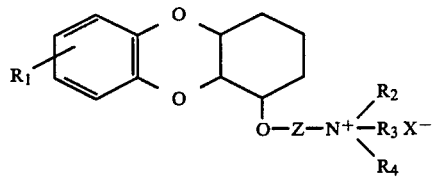

in which $R_1$ denotes H, halogen or a linear or branched $C_1$ to $C_3$ alkoxy or alkyl group, $R_2$, $R_3$ and $R_4$ separately denote a linear or branched $C_1$ to $C_4$ alkyl group or $R_2$ and $R_3$ together with the nitrogen atom to which they are bound form a saturated heterocyclic radical, Z denotes a linear or branched $C_1$ to $C_6$ alkylene group and $X^-$ denotes an anion, preferably a halogen ion, and is dealing with intermediates in the preparation of the compounds of formula I.

10 Claims, No Drawings

HEXAHYDRODIBENZODIOXANE COMPOUNDS AND PHARMACEUTICAL COMPOSITIONS

The present invention has as its subject new ammonium salts derived from 1,2,3,4,4a,10a-hexahydrodibenzo[b,e][1,4]-dioxin-4-ol, the intermediates necessary for their preparation and their application in therapy. More particularly the new compounds correspond to the formula (I)

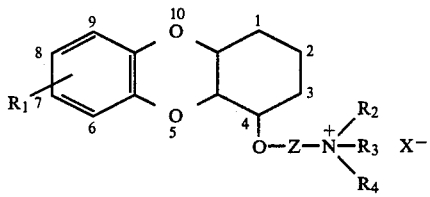

in which $R_1$ denotes H, halogen or a linear or branched $C_1$ to $C_3$ alkoxy or alkyl group, $R_2$, $R_3$ and $R_4$ separately denote a linear or branched $C_1$ to $C_4$ alkyl group or $R_2$ and $R_3$ together with the nitrogen atom to which they are bound form a saturated heterocyclic radical, Z denotes a linear or branched $C_1$ to $C_6$ alkylene group and $X^-$ denotes an anion, preferably a halogen ion.

By linear or branched $C_1$ to $C_6$ alkyl, there are understood methyl, ethyl, propyl, isopropyl and the butyl, pentyl and hexyl groups; for $R_4$ the methyl group is preferred, for Z the ethyl group, while for $R_2$ and $R_3$ isopropyl groups are preferred.

By a saturated heterocyclic radical represented by $NR_2R_3$, there are understood a morpholino, piperidino or pyrrolidino group.

A halogen anion is to be understood as $Cl^-$, $Br^-$, $I^-$; whereby bromine is the preferred ion.

The compounds of formula (I) can be prepared by performing the following reactions:
(a) reaction of an alcohol of formula (II)

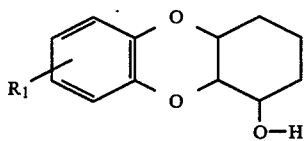

with a haloalkylamine of the formula:

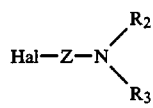

in which $R_1$, Z, $R_2$ and $R_3$ have the significance given above, and Hal represents halogen, under conventional conditions, preferably in the presence of a base. For example, it is possible to work in an inert organic solvent in the presence of NaH, t-BuOK or an alkali metal alcoholate, but it is preferred to carry out this etherification in the presence of sodium hydroxide in concentrated aqueous solution and a phase transfer catalyst, without solvent or in a solvent such as benzene or toluene.
(b) reaction of the amine obtained above of the formula (III)

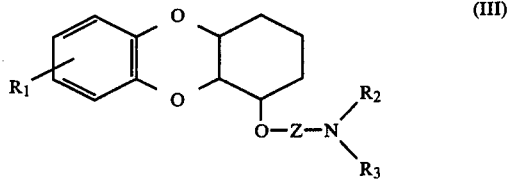

with a compound of the formula $X—R_4$ under conventional conditions, whereby $R_4$ has the meaning defined above and X represents the group that forms the anion $X^-$ after the reaction, X preferably being halogen.

If desired, the anion $X^-$ of the compound thus obtained may be exchanged for another suitable anion $(X^-)$ by methods well known in the literature.

The compounds of the formula (II) are, to the best of Applicant's knowledge, new compounds which are useful as intermediates in the synthesis of various types of compounds having, in particular, therapeutic activity. They are prepared in two stages:
(a) by reaction of 3-halocyclohexene with an orthohydroxybenzaldehyde in the presence of a base

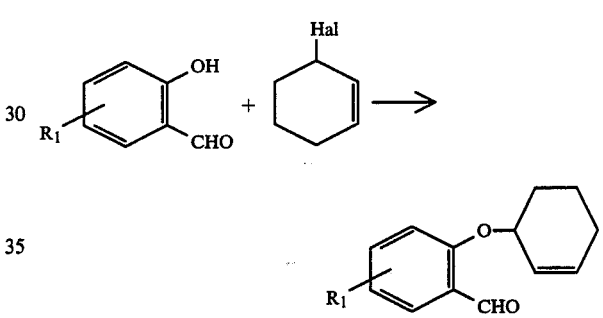

followed by cyclisation by
(b) the action of a peracid and then of a strong base on the compound obtained followed by treatment with methylamine:

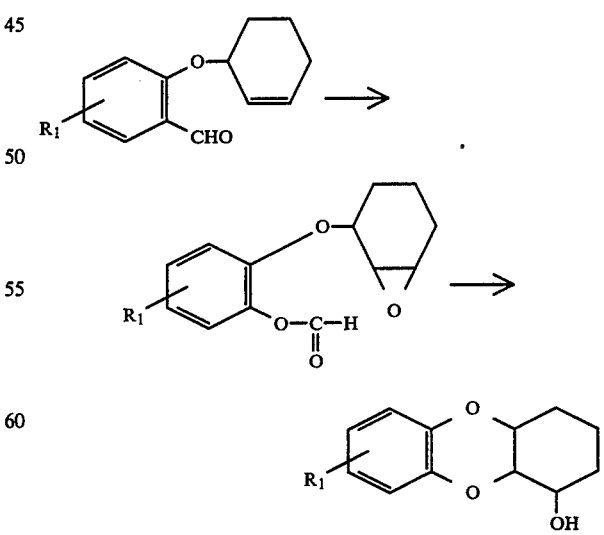

Stage (a) can be carried out with 3-bromocyclohexene and it is then possible to work advantageously in the presence of potassium carbonate at room temperature in acetone; stage (b) is accomplished, for example, by the action of meta-chloroperbenzoic acid in a chlorinated solvent such as dichloromethane, the reaction medium is then treated with a concentrated alkali metal hydroxide solution and the mixture obtained after removal of the solvents is then treated with methylamine in alcoholic solution.

The quaternary ammonium compounds of formula (I) have pharmacological activities, in particular potent antispasmodic activity. Further subjects of the invention are the pharmaceutical compositions containing at least one of the compounds of formula (I) as active principle. These pharmaceutical compositions will be useful in human therapy, in particular in the treatment of spasmodic syndromes.

The following examples describe the preparation of compounds according to the invention, and the results obtained for certain compounds in conventional pharmacological tests.

EXAMPLE 1

1,2,3,4,4a,10a-hexahydrodibenzo[b,e][1,4]-dioxin-4-ol

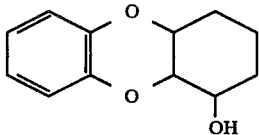

In a 10-liter reactor there were introduced 633.4 g (5.19 moles) of salicylaldehyde, 5 liters of acetone and 717.3 g of potassium carbonate, and the mixture was left with stirring at room temperature. After precipitation of the phenate, 836 g (5.19 moles) of 3-bromocyclohexene were rapidly added dropwise, and the mixture was brought to reflux for 2½ hours. After removal of the inorganic salts by filtration, and evaporation of the solvent, the residue was taken up in ethyl ether, washed with 10% caustic soda and then water, and the ether phase was then dried over Na₂SO₄. After filtration and elimination of the ether, there were obtained 975 g of 3-(2-formylphenoxy)cyclohexene, which was used directly in the following stage.

In a second stage, there were introduced in a 10-liter reactor maintained in an icebath 2,159 g (12,5 moles) of meta-chloroperbenzoic acid and 5 liters of dichloromethane, 975 g of the above compound dissolved in 1 liter of dichloromethane were then added dropwise, and the temperature was maintained below 30° C. while the reaction was allowed to continue for 1 hour. The acid formed was then filtered off and the filtrate reintroduced into the reactor; while maintaining the temperature below 30° C., 1,000 g of 50% (12.5M) caustic soda solution was added dropwise. After the mixture was left for one hour with stirring at room temperature, the organic phase was separated and washed with water, dried over Na₂SO₄ and filtered, the solvent was evaporated and the concentrate was then taken up in 1 liter of absolute ethanol and 0.5 liter of a 33% alcoholic solution of methylamine and the mixture was brought to reflux for 3 hours. The ethanol was then evaporated, the residue was taken up in ethyl ether, and the solution washed with water, dried over Na₂SO₄, filtered and then concentrated to dryness. On addition of pentane the compound of the title crystallises. There were thus obtained 587.15 g of product of melting point 81°–82° C., having the elementary analysis:

|  | C % | H % |
| --- | --- | --- |
| Calculated | 69.88 | 6.84 |
| Found | 69.84 | 6.85 |

EXAMPLE 2

9-methoxy-1,2,3,4,4a,10a-hexahydrodibenzo-[b,e][1,4]dioxin-4-ol

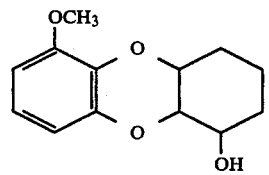

In an analogous manner as described in Example 1, but starting with 64 g of 2-hydroxy-3-methoxybenzaldehyde, there are obtained 29 g of the title-compound of boiling point 225° C. at a pressure of 6.5 Pa, having the elementary analysis:

|  | C % | H % |
| --- | --- | --- |
| Calculated | 66.08 | 6.82 |
| Found | 65.99 | 6.83 |

EXAMPLE 3

4-(2-morpholinoethoxy)-1,2,3,4,4a,10a-hexahydrodibenzo[b,e][1,4]dioxin

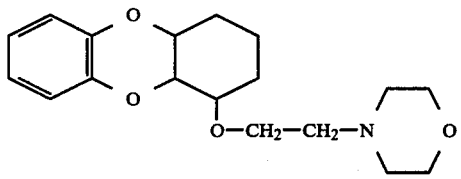

In a 10-liter reactor there were introduced 6 kg of 50% caustic soda solution, 1,150 g (5.576 moles) of the alcohol of Example 1, 986 g (5.3 moles) of 4-(2-chloroethyl)morpholine hydrochloride and 0.5 g of crown ether 18-crown-6 (1,4,7,10,13,16-hexaoxacyclooctadecane), and the mixture was then brought to 120° C. for 5 hours with stirring. After being cooled, the mixture was extracted with ether and the extract was washed with water dried over Na₂SO₄ and filtered, the solvent was evaporated and the product distilled under vacuum. There were thus obtained 1,330 g of the title-compound of boiling point 180° C. at a pressure of 65 Pa, having the elementary analysis:

|  | C % | H % | N % |
| --- | --- | --- | --- |
| Calculated | 67.69 | 7.89 | 4.38 |
| Found | 67.70 | 8.12 | 4.35 |

EXAMPLE 4

4-(2-morpholinoethoxy)-9-methoxy-1,2,3,4,4a,10a-hexahydrodibenzo-[b,e][1,4]dioxin

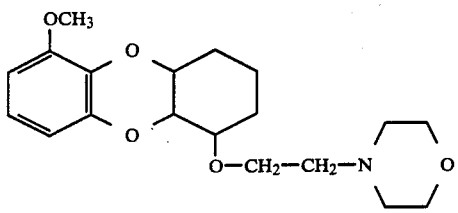

In an analogous manner as described in Example 3, but starting with 10 g (0.042 mole) of the alcohol of Example 2 and 9 g (0.038 mole) of 4-(2-chloroethyl)-morpholine hydrochloride, there were obtained 7.4 g of the title-compound of boiling point 192°–195° C. at a pressure of 65 Pa, having the elementary analysis:

|  | C % | H % | N % |
| --- | --- | --- | --- |
| Calculated | 65.31 | 7.79 | 4.01 |
| Found | 64.98 | 7.80 | 3.97 |

EXAMPLE 5

4-(2-diisopropylaminoethoxy)-1,2,3,4,4a,10a-hexahydrodibenzo-[b,e][1,4]dioxin

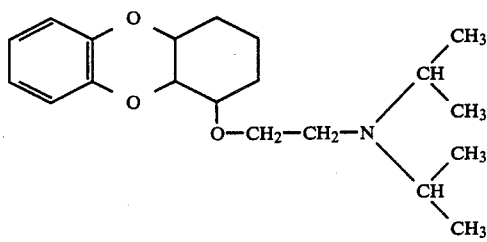

Working as described in Example 3, but starting with 12.4 g (0.06 mole) of the alcohol of Example 1 and 10 g (0.05 mole) of 1-chloro-2-diisopropylaminoethane hydrochloride, there were obtained 13.7 g of the title-compound of melting point 63.4° C., having the elementary analysis:

|  | C % | H % | N % |
| --- | --- | --- | --- |
| Calculated | 72.03 | 9.37 | 4.20 |
| Found | 72.04 | 9.31 | 4.19 |

EXAMPLE 6

4-(3-dimethylaminopropoxy)-1,2,3,4,4a,10a-hexahydrodibenzo-[b,e][1,4]dioxin

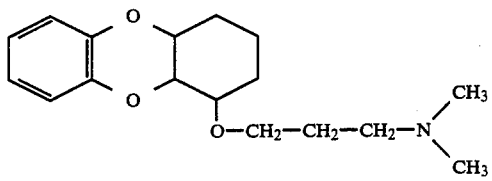

In an analogous manner as described in Example 5, but starting with 10 g (0.048 mole) of the alcohol of Example 1 and 6.6 g (0.042 mole) of 3-dimethylamino-1-chloropropane hydrochloride, there were obtained 6.8 g of the title-compound of boiling point 165° C. at a pressure of 1.33 Pa, having the elementary analysis:

|  | C % | H % | N % |
| --- | --- | --- | --- |
| Calculated | 70.07 | 8.65 | 4.81 |
| Found | 68.93 | 8.78 | 4.76 |

EXAMPLE 7

4-(2,2-dimethyl-3-dimethylaminopropoxy)-1,2,3,4,4a,10a-hexahydrodibenzo[b,e][1,4]dioxin

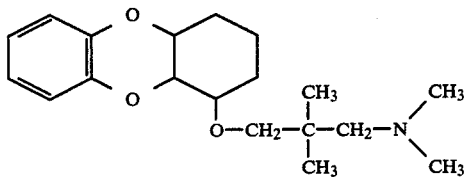

In an analogous manner as described in Example 5, but starting with 10 g (0.048 mole) of the alcohol of Example 1 and 8.6 g (0.046 mole) of 1-chloro-2,2-dimethyl-3-dimethylaminopropane hydrochloride, there were obtained 8.6 g of the title-compound of boiling point 135° C. at a pressure of 6.5 Pa, having the elementary analysis:

|  | C % | H % | N % |
| --- | --- | --- | --- |
| Calculated | 71.44 | 9.15 | 4.38 |
| Found | 71.57 | 9.18 | 4.31 |

EXAMPLE 8

N-{2-(1,2,3,4,4a,10a-hexahydrodibenzo[b,e][1,4]dioxin-4-yloxy)ethyl}-N-methylmorpholinium bromide In an autoclave, 900 g (2.82 moles) of the amino ether of Example 3 were dissolved in 3 liters of acetone, and 535.6 g (5.64 moles) of methyl bromide were added. After crystallisation had started, the mixture was left with stirring for 2 hours at room temperature. After being filtered and rinsed with acetone, the solid formed was resuspended in petroleum ether, stirring, filtered, dried under vacuum and then recrystallised in a minimum quantity of the mixture diisopropyl ether/isopropanol (7:3). There were thus obtained 1000 g of the title-compound of melting point 155° C., having the elementary analysis:

|  | C % | H % | N % |
| --- | --- | --- | --- |
| Calculated | 55.07 | 6.81 | 3.38 |
| Found | 55.40 | 6.80 | 3.37 |

EXAMPLE 9

N-{2-(9-methoxy-1,2,3,4,4a,10a-hexahydrodibenzo[b,e][1,4]dioxin-4-yloxy)ethyl}-N-methylmorpholinium bromide Following the same procedure as in Example 8, 3.5 g (0.01 mole) of the amino ether of Example 4 were used at the start to obtain, after the action of methyl bromide, 3.3 g of the title-product of melting point 167.1° C., having the elementary analysis:

|  | C % | H % | N % |
|---|---|---|---|
| Calculated | 54.06 | 6.81 | 3.15 |
| Found | 53.89 | 6.90 | 3.13 |

EXAMPLE 10

N-{2-(1,2,3,4,4a,10a-hexahydrodibenzo[b,e][1,4]dioxin-4-yloxy)ethyl}-N-methyl-N,N-diisopropylammonium bromide Following the same procedure as in Example 8, starting with 5.6 g (0.017 mole) of the amino ether of Example 5, there were obtained 4.5 g of the product of the title of melting point 155.5° C., having the elementary analysis:

|  | C % | H % | N % |
|---|---|---|---|
| Calculated | 58.87 | 8.00 | 3.27 |
| Found | 58.06 | 8.15 | 3.21 |

EXAMPLE 11

N-{2-(1,2,3,4,4a,10a-hexahydrodibenzo[b,e][1,4]dioxin-4-yloxy)ethyl}-N-methylmorpholinium iodide In an analogous manner as described in Example 8 but starting with 600 g (1.88 moles) of the compound of Example 3 and 537.4 g (3.76 moles) of methyliodide, there were obtained 561 g of the title-compound with melting point 162° C.

The quaternary ammonium compounds of formula (I) were shown to possess useful antispasmodic properties, which were demonstrated in vitro by the customary methods of molecular pharmacology. For anticholinergic activity, acetylcholine was used as agonist and rat jejunum as biological effector. For antihistaminic activity and for inhibitory activity on $BaCl_2$-induced membrane permeability, histamine and $BaCl_2$ were used, respectively, and guinea pig ileum as biological effector. The characteristic $pA_2$ values of the substances studied, calculated according to the method of VAN ROSSUM [Arch. int. Pharmacodyn. 143 299–330 (1963)], are recorded in the table below:

| Compound of Example No. | Anti-cholinergic activity | Anti-histaminic activity | Membrane permeability inhibition |
|---|---|---|---|
| 8 | 5.45 ± 0.151 | 5.5 ± 0.24 | 5.0 ± 0.22 |
| 9 | 4.6 ± 0.10 | inactive at $10^{-4}$ M | 4.1 (at $10^{-4}$ M only) |
| 10 | 6.1 ± 0.12 | 4.1 ± 0.11 | 5.3 ± 0.35 |

These results show that the compounds of the invention possess useful antispasmodic properties, compound No. 8 having comparable levels of activity towards the three agonists used. These compounds furthermore have very low toxicity. At 640 mg/kg, administered orally in mice, no mortality was noted: the $LD_{50}$ may therefore be estimated as $\geq 2$ g/kg per os.

Their use in human or animal therapy can hence be envisaged in the treatment of spasmodic conditions of all origins. Associated with the usual pharmaceutical excipients, they may be administered enterally or parenterally at daily doses between 0.1 mg and 15 mg/kg body weight depending on the method of administration. For the treatment of humans a daily dosage of between 10 mg and 1000 mg may be used, whereby the oral route of administration is preferred.

Mixed with suitable auxiliaries the compounds I or a salt thereof may be compressed into solid dosage units such as pills, tablets etc., or may be processed into capsules. By means of suitable liquids the compounds may also be applied as an injection- or oral-preparation in the form of solutions, suspensions or emulsions.

The compounds of formula I possess a chiral carbon, as a result of which a racemic mixture I and separate optical enantiomers I are possible. Both the racemic mixture, as well as the separate optical enantiomers belong to the compounds according to the invention. The separate optical enantiomers can be prepared in the usual manner by resolution of the racemic mixture or directly using optically active starting products.

We claim:

1. Compounds of the formula I

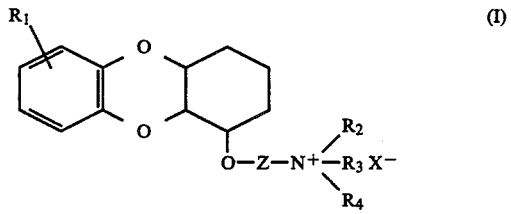

in which $R_1$ denotes H, halogen or a linear or branched $C_1$ to $C_3$ alkoxy or alkyl group, $R_2$, $R_3$ and $R_4$ separately denote a linear or branched $C_1$ to $C_4$ alkyl group or $R_2$ and $R_3$ together with the nitrogen atom to which they are bound form a saturated heterocyclic radical, Z denotes a linear or branched $C_1$ to $C_6$ alkylene group and $X^-$ denotes an anion.

2. Compounds according to claim 1 in which Z denotes $-CH_2-CH_2-$.

3. Compounds according to claim 1 in which $R_2$ and $R_3$ denote isopropyl.

4. Compounds according to claim 1 in which

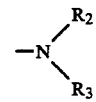

denotes the morpholino radical.

5. Compounds according to claim 1 in which $R_4$ denotes methyl.

6. Compounds according to claim 1 in which $X^-$ denotes halogen ion.

7. Pharmaceutical composition for antispasmodic activity, characterised in that it contains at least one of the compounds according to claim 1, together with one or more usual pharmaceutical auxiliaries.

8. Pharmaceutical composition according to claim 7, characterised in that it contains, as the active principle, the compound of formula
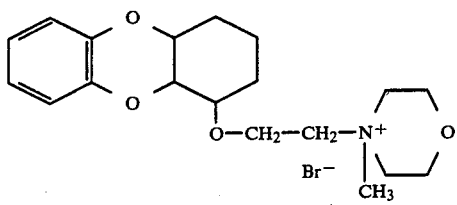
9. A compound of the formula III
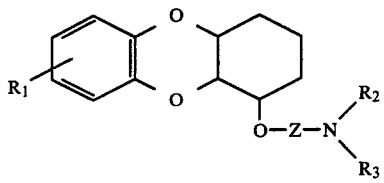
in which $R_1$, Z, $R_2$ and $R_3$ have the meanings defined in claim 1.
10. Compounds according to claim 14 in which $X^-$ denotes $Br^-$.